(12) United States Patent
Laiosa et al.

(10) Patent No.: US 10,265,476 B2
(45) Date of Patent: Apr. 23, 2019

(54) TWO BODY SYRINGE CARRIER ASSEMBLY WITH DAMPENER

(71) Applicant: SHL GROUP AB, Nacka Strand (SE)

(72) Inventors: John Laiosa, Lodi, CA (US); Dane Kris, Deerfield Beach, FL (US); Slobodan Stefanov, Deerfield Beach, FL (US)

(73) Assignee: SHL MEDICAL AG, Zug (CH)

( * ) Notice: Subject to any disclaimer, the term of this patent is extended or adjusted under 35 U.S.C. 154(b) by 371 days.

(21) Appl. No.: 15/068,467

(22) Filed: Mar. 11, 2016

(65) Prior Publication Data
US 2017/0259002 A1    Sep. 14, 2017

(51) Int. Cl.
A61M 5/20 (2006.01)
A61M 5/31 (2006.01)
A61M 5/32 (2006.01)

(52) U.S. Cl.
CPC ........ A61M 5/3129 (2013.01); A61M 5/2033 (2013.01); A61M 5/326 (2013.01); A61M 5/3204 (2013.01); A61M 2005/206 (2013.01); A61M 2005/208 (2013.01); A61M 2005/2013 (2013.01); A61M 2005/3143 (2013.01); A61M 2005/3267 (2013.01)

(58) Field of Classification Search
CPC ................ A61M 5/2033; A61M 5/326; A61M 2005/2013; A61M 5/3129
USPC ......................................................... 604/136
See application file for complete search history.

(56) References Cited

U.S. PATENT DOCUMENTS

| 8,496,619 B2 * | 7/2013 | Kramer ............... A61M 5/2033 604/135 |
| 2005/0101919 A1 | 5/2005 | Brunnberg |
| 2007/0135767 A1 | 6/2007 | Gillespie et al. |
| 2014/0257191 A1 | 9/2014 | Cowe |
| 2016/0008542 A1 | 1/2016 | Hirschel et al. |

FOREIGN PATENT DOCUMENTS

| EP | 2468341 A1 | 6/2012 |
| WO | 2011/032731 A1 | 3/2011 |

* cited by examiner

*Primary Examiner* — Phillip A Gray
(74) *Attorney, Agent, or Firm* — McDonnell Boehnen Hulbert & Berghoff LLP (57) ABSTRACT

A two body syringe carrier assembly for use in an injection device is presented where a force dampener is operatively connected to the two bodies to dissipate spring force at the completion of the penetration and/or injection steps. The injection device has a generally elongated tubular housing, a syringe containing medicament and having a needle, a needle shield slidably arranged to the housing and protruding a distance outside the front end of the housing, a plunger arranged to act on the syringe and a pre-tensioned drive member arranged the drive the plunger.

17 Claims, 9 Drawing Sheets

TWO BODY SYRINGE CARRIER ASSEMBLY WITH DAMPENER

FIELD OF THE INVENTION

The present invention relates to an drug delivery device for administering drugs in a safe and reliable way. More specifically, the drug delivery device concerns an auto-injector for delivery a dose of medicament from a prefilled syringe using a moving syringe carrier.

BACKGROUND

The handling and safety aspects of injector devices, having a certain degree of automatic functions, as well as immediate accessibility in emergency situations are issues that attract a lot of attention when developing this type of device. These devices typically rely on compressive spring forces that are released during the triggering of the device to cause the injection. One issue with these automated injection devices is the potential for the user to experience a negative tactile feeling as the needle penetration step and/or injection sequence is completed. This is sometimes referred to as "kick-back" and is a result of the excess spring forces being transferred from the device to the injection site. A goal of designers of these rug delivery devices is to minimize or eliminate these forces from being transferred or felt by the user of the device.

One known auto-injection device is described in the co-owned U.S. Pub. No. 2005/0101919, however, whereby the injection can be activated by a push button, i.e. penetration and injection, but only when the front end of the injector is pressed against the injection site. It is designed as a kind of two-step operation where the order has to be: pressing the injector at the site and then depressing the button. This ensures that the injector cannot be accidentally activated by merely pushing the button nor even pushing the button and then pressing the front end. This device however has no features to eliminate or reduce the transfer of excess spring force at the completion of the penetration step and/or injection step.

SUMMARY

The aim of the invention is to provide an injection device, preferably an auto-injector, which is uncomplicated and easy to use, which is safe both before, during and after use and which displays a high degree of functionality. Another aim is to minimize or eliminate the negative tactile feel experienced by the user at the completion of the penetration and/or injection steps. The injection device may contain an injection button that is activated only when a needle shield is pushed against the injection site. In alternative embodiment, the injection device does not include a button and is activated when pushed against the injection site.

According to one aspect of the invention, a syringe carrier assembly is disclosed having an inner body and an outer body that are rotationally fixed to each other both cooperate to allow relative axial movement. The syringe carrier assembly further comprises a force dampener that absorbs and dissipates spring force during the operation of an injection device.

More particularly, the syringe carrier assembly is for use in an auto-injector. The inner body has a proximal end, a distal end and an outer surface, where the inner body is formed as a hollow tubular shape configured to accept and hold a syringe, preferably a pre-filled syringe, from axial movement relative to the inner body. The outer body has a hollow interior sized to accept and surround the inner body, where the outer body and inner body are slideably connected to each other such that inner body and the outer body are rotationally fixed to each other while allowing relative axial movement. A force dampener is also part of the assembly and is operatively connected to both the inner body and the outer body to dissipate excess spring force from the pre-tensioned helical compression spring that when released drives the syringe carrier assembly and the plunger forward in a proximal direction when the inner body moves axially relative to the outer body during a dose delivery operation of the auto-injector.

In one aspect of the invention the force dampener comprises a dampener ring surrounding a portion of the outer surface of the inner body and positioned relative to the outer body such that axial movement of the inner body relative to the outer body causes compression of the dampener ring to stop the axial movement of the inner body and to dissipate the spring force.

In another aspect, the force dampener comprises a combination of a longitudinal array of axial spaced ratchet teeth and a flexible rib comprising a ratchet tooth configured to engage with the array of axial spaced ratchet teeth such that axial movement of the inner body relative to the outer body causes the ratchet tooth to ride up and over the array of of axial spaced ratchet teeth to dissipate the spring force. The longitudinal array of axial spaced ratchet teeth can be located on the outer surface of the inner body. The flexible rib can be part of the outer body such that the ratchet tooth projects radially into the hollow interior. The distal end of the inner body can also have a flange containing a step portion that provides a distal bearing surface for abutment with a syringe flange when a syringe is positioned within the inner body. The inner body flange can have two distally directed tongues.

The slideable connection between the two bodies comprises a cooperation of a raised spline located on one of the inner body and outer body with a correspondingly shaped longitudinal channel on one of the inner body and outer body. These longitudinal splines mate with cooperating channels located on an inside surface of the outer body to prevent relative rotation, but allow axial movement, between the inner body and the outer body.

In one embodiment where the force dampener is the dampener ring it is located at the distal end of the inner body abutting a flange. The longitudinal splines are located along the outer surface of the inner body terminating prior to a flange located at the distal end of the inner body to define a gap that accepts the dampener ring when positioned on the outer surface abutting the flange. The outer body in this embodiment has a cup portion at a distal end configured to contain the dampener ring and to prevent the dampener ring from moving axially relative to the inner body. The cup portion has an internal diameter greater than an outer diameter of the flange such that the dampener ring and flange fit within the cup portion of the outer body. This flange is configured as a bearing surface for the syringe.

In another aspect of the present disclosure there is disclosed a drug delivery device comprising an outer housing, one of the previously disclosed syringe assemblies, and a pre-filled syringe containing a dose of medicament positioned within the syringe assembly. A method of performing an injection of a dose of medicament using this drug delivery device includes pressing a needle shield positioned within the outer housing against an injection site, pushing an activation button located at a distal end of the outer housing, releasing a pre-tensioned compression spring within the outer housing to move the syringe carrier assembly axially in a proximal direction, and stopping axial movement of the the outer body while allowing the inner body to continue moving axially to engage and activate the force dampener.

The injection device containing the syringe assemblies disclosed herein comprises a generally elongated tubular housing, a container containing medicament and having a needle attached to the container, a needle shield slidably arranged to the housing and protruding a distance outside the front end of said housing, a plunger arranged to act on said container and a pre-tensioned drive means arranged to drive said plunger, characterized in that it comprises radially acting holding means capable of releasably holding said plunger, axially acting actuator means connected to said needle shield and capable of releasably locking said holding means and axially acting activator means capable of releasing said holding means from said actuator means when said needle shield and said actuator means has moved axially a certain distance because the injection device has been placed and pressed against an injection site.

The injector according to the present invention comprises a number of radially and axially co-acting means in order to obtain a compact and yet reliable injecting device with rather few components. This implies that the holding means are acting to hold and lock the pre-tensioned plunger radially which is a safe way to lock and store the device pre-tensioned for long periods until use. As a benefit the user does not have to arm the device before use. The holding means are held in place by the axially slidable actuator means, preferably a sleeve, which in turn is connected to the needle shield. Thus the movement of the needle shield, when pressing the device against an injection site axially moves the actuator sleeve axially in relation to the holding means, but not so much that the holding means is released from the plunger. This step of releasing the plunger is performed by the activator means, for example a push button at the end of the device, which moves the holding means axially in relation to the actuator sleeve until the holding means is released and the plunger is released to act on the container.

The axial movement in order to release the holding means is thus performed both by the actuator sleeve but also by the holding means. There is thus a two-step operation in order to activate an injection. For enhancing the safety of the device it is designed so that the operation of the device is performed in a pre-determined sequence.

The needle shield is further provided with a spring that urges needle shield to an extended position surrounding the needle when the device is withdrawn from the injection site after the injection, and locking means for locking the needle shield in that extended position in order to avoid accidental needle sticks after injection and subsequently after disposal. The device may be provided with means for delivering a subsequent dose, whereby the needle first has to be removed and replaced. In order to enable this the needle shield can be released by a separate release mechanism in order to push it backwards, or with a separate tool, thereby exposing the needle so that it can be replaced.

The device may also be arranged for replaceable containers, i.e. when one container is emptied, the patient replaces it with a new container.

The mechanism of the injector of the present invention is designed such that an injection is only activated when first the injector is pressed against the injection site and then the activator (e.g. a button) is pressed or activated. It is not possible to press the activator first and then press the injector against an object to activate an injection nor is it possible to perform these steps simultaneously. Also if the injector is removed from an injection site before the activator is pressed, the injector is reset to its original locked state. This ensures a very high degree of safety in handling the device and prevention of faulty or not performed injections.

These and other aspects of and advantages with the present invention will become apparent from the following detailed description and from the accompanying drawings.

BRIEF DESCRIPTION OF THE FIGURES

In the following detailed description of the invention, reference will be made to the accompanying drawings, of which

DETAILED DESCRIPTION

The drug delivery device 100 shown in the drawings comprises a front or proximal end 10 and a rear or distal end 61.

Figure 1:
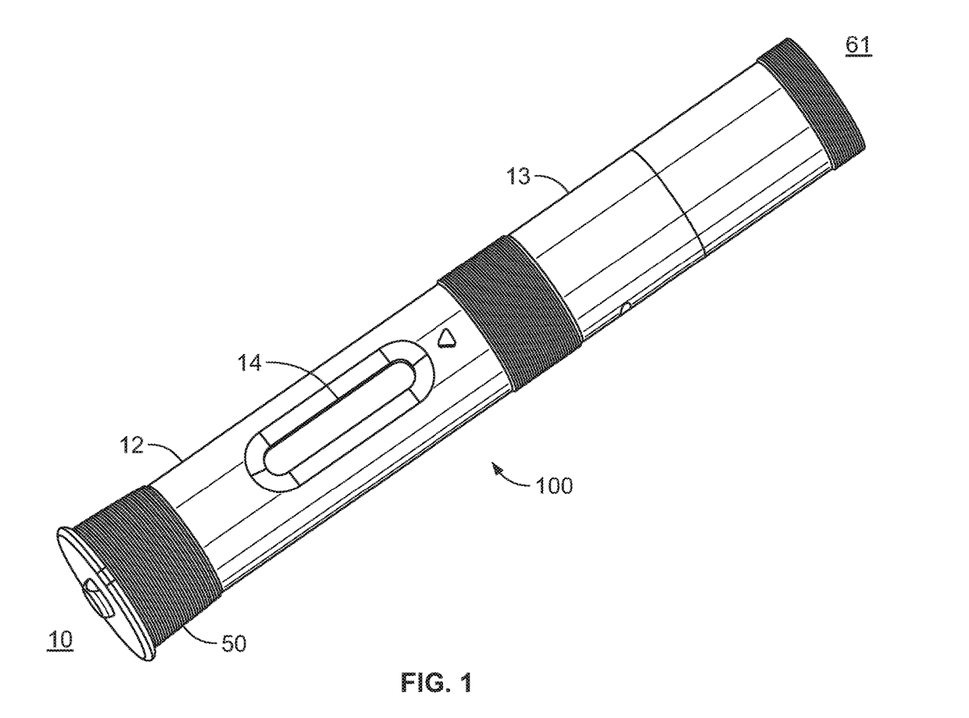
FIG. 1 is a perspective view of the drug delivery device of one embodiment of the present disclosure.
Figure 2A:
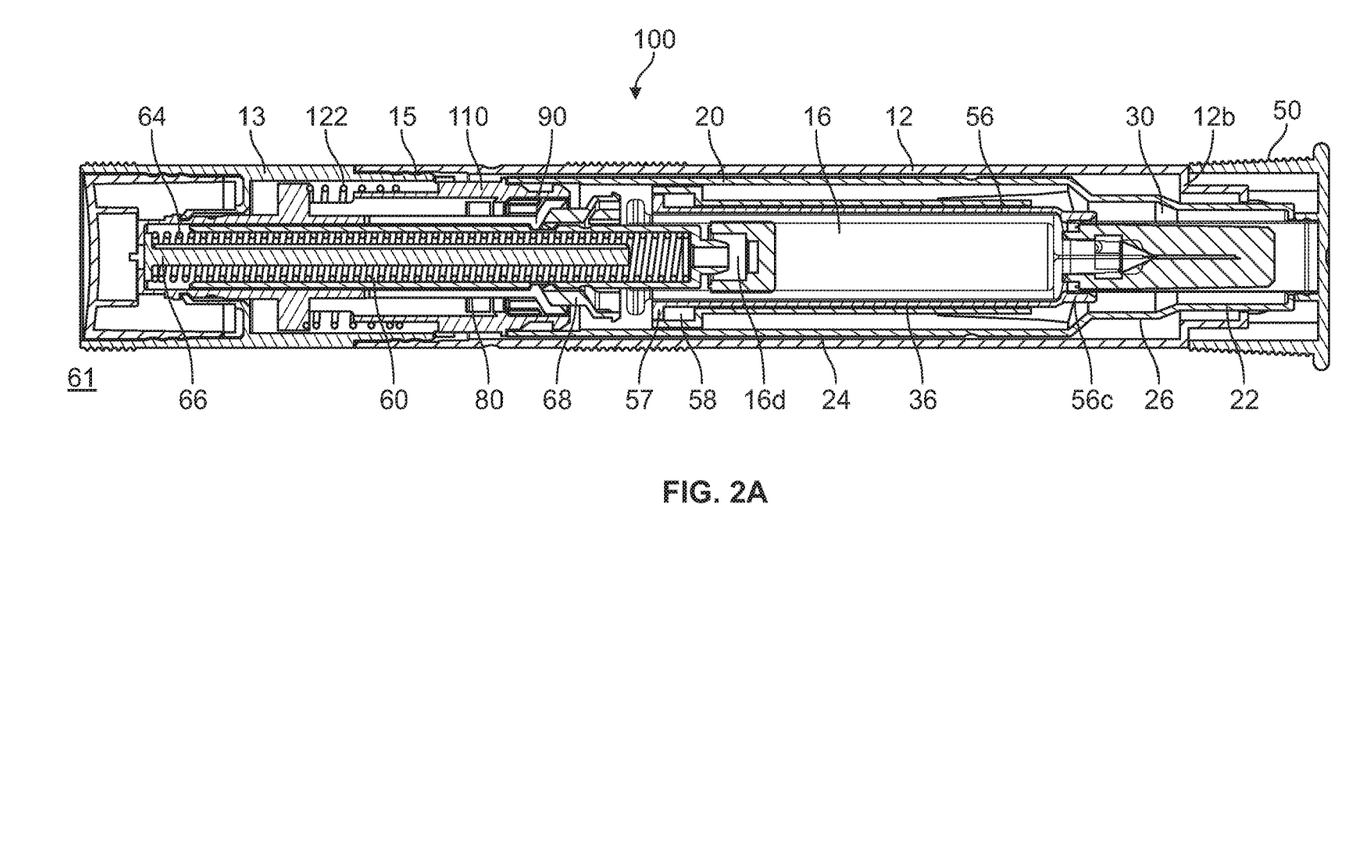
FIG. 2a is a cross-sectional view of the drug delivery device according to FIG. 1 showing a first embodiment of the syringe carrier assembly of the present disclosure.
Figure 2B:
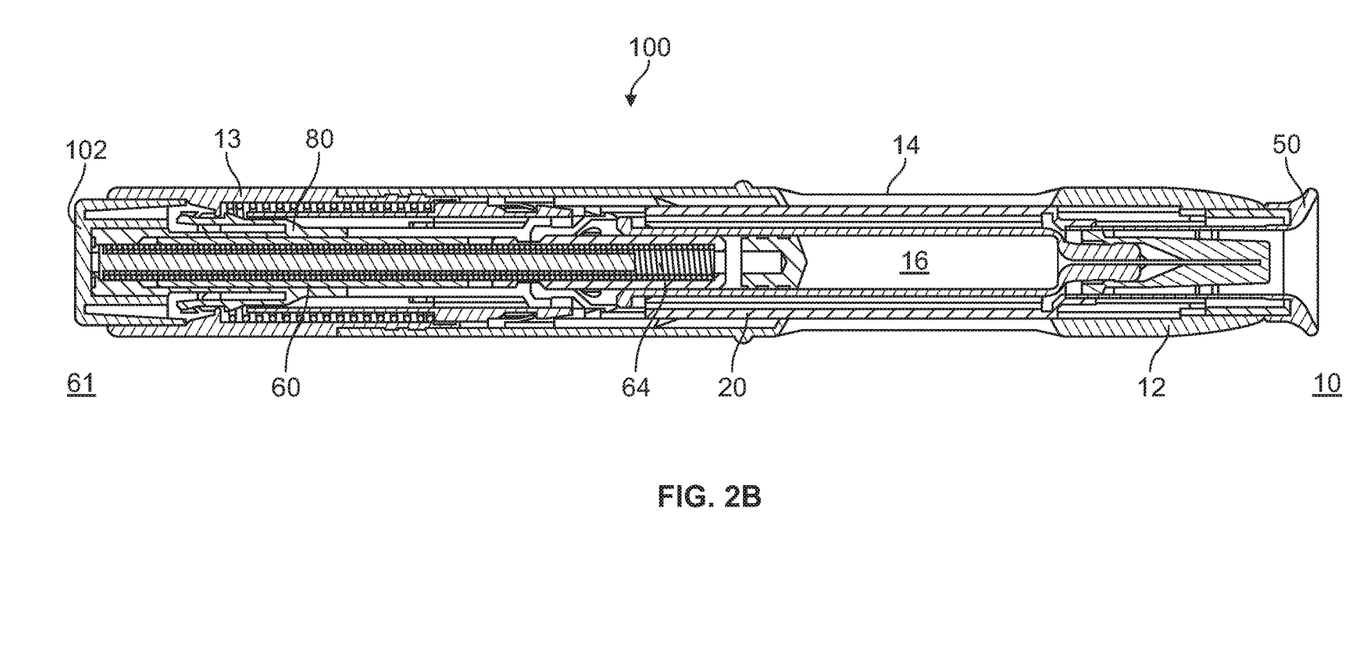
FIG. 2b is a cross-sectional view of an alternative embodiment of the drug delivery device that includes a button 102 that activates the device provided the needle shield is pressed against the injection site.
Figure 3:
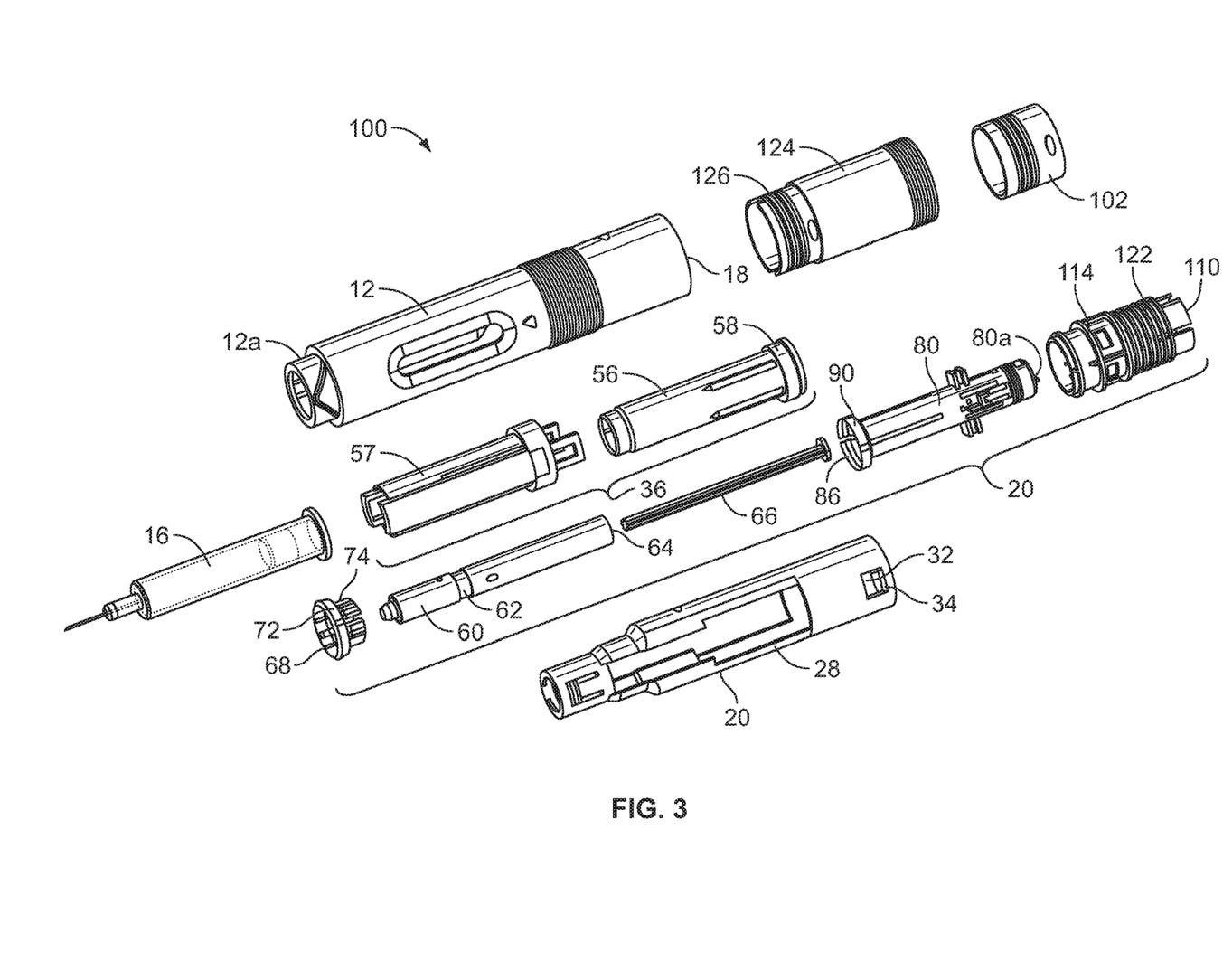
FIG. 3 is an exploded view of the of the drug delivery device shown in FIGS. 1 and 2.

The front end 10 comprises a generally tubular front body 12 having elongated openings 14 for viewing a syringe 16 as shown in FIGS. 1 and 2b and having a somewhat narrowing front end 12a (see FIG. 3). The rear end 61 of device 100 has a rear tubular rear body 13 that is joined with front body 12 with connection 15 (see FIG. 2a), where one part of the connection 15 is on the front body 12 and the cooperating and mating connector is on the rear body 13. Inside the front body 12 is a needle shield 20 that is axially slidably arranged. The needle shield 20 is generally tubular with a first front part 22 having a certain diameter and a second rear part 24 having a diameter larger than the front part 22, where these parts are joined by an intermediate conical part 26. Two elongated grooves 28 are arranged along the needle shield 20, on opposite sides of the needle shield 20, also for viewing the syringe and guiding axial movement of the outer body 57. On the inner surface of the conical part 26 a circumferential ledge 30 is arranged. At the rear end of the needle shield 20 two openings 32 are arranged opposite each other, where each opening 32 is arranged with somewhat inwardly projecting, flexible, tongues 34.

Figure 4:
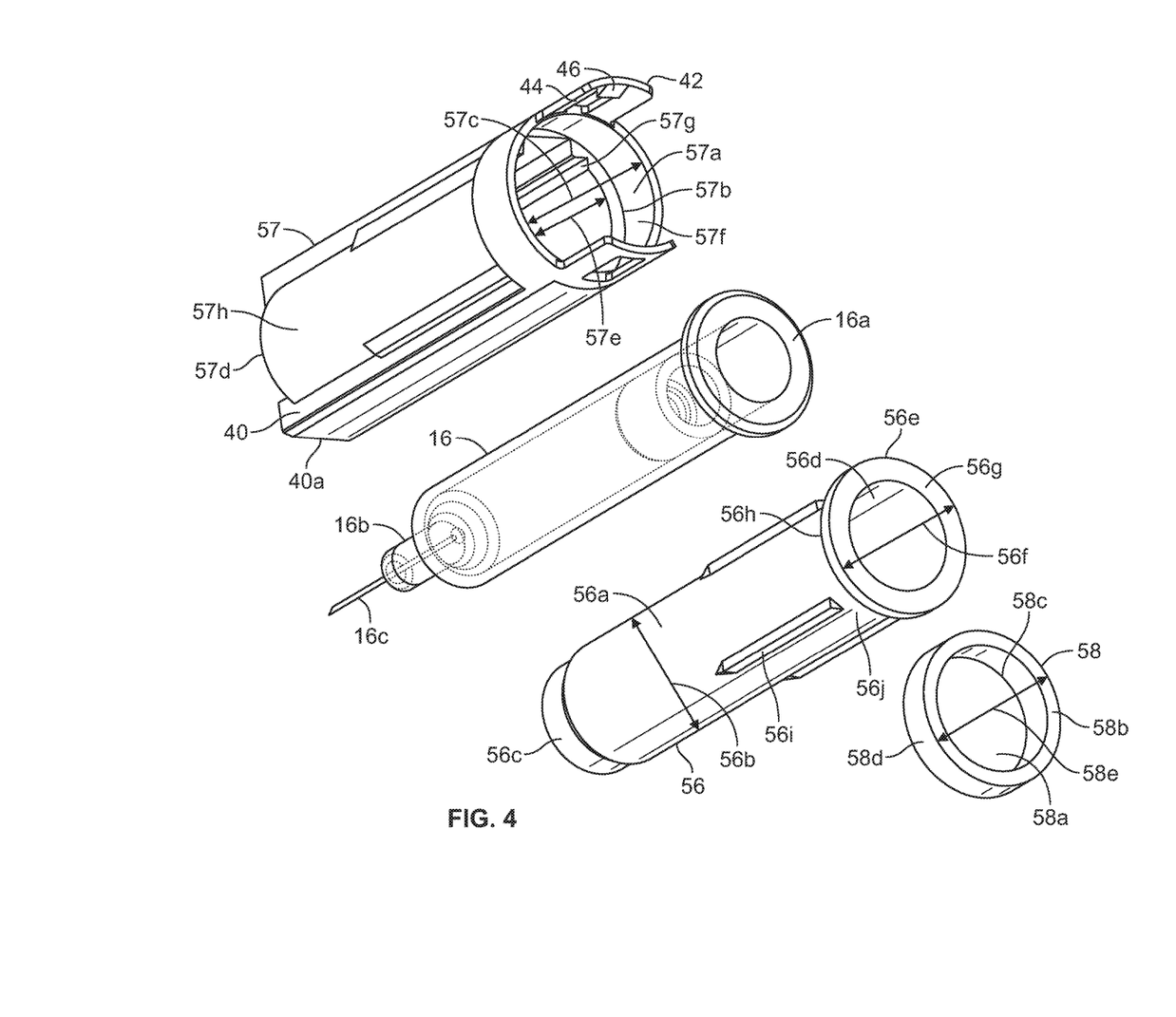
FIG. 4 is an exploded view of the syringe carrier assembly and prefilled syringe of the drug delivery device according to FIG. 2.
Figure 5:
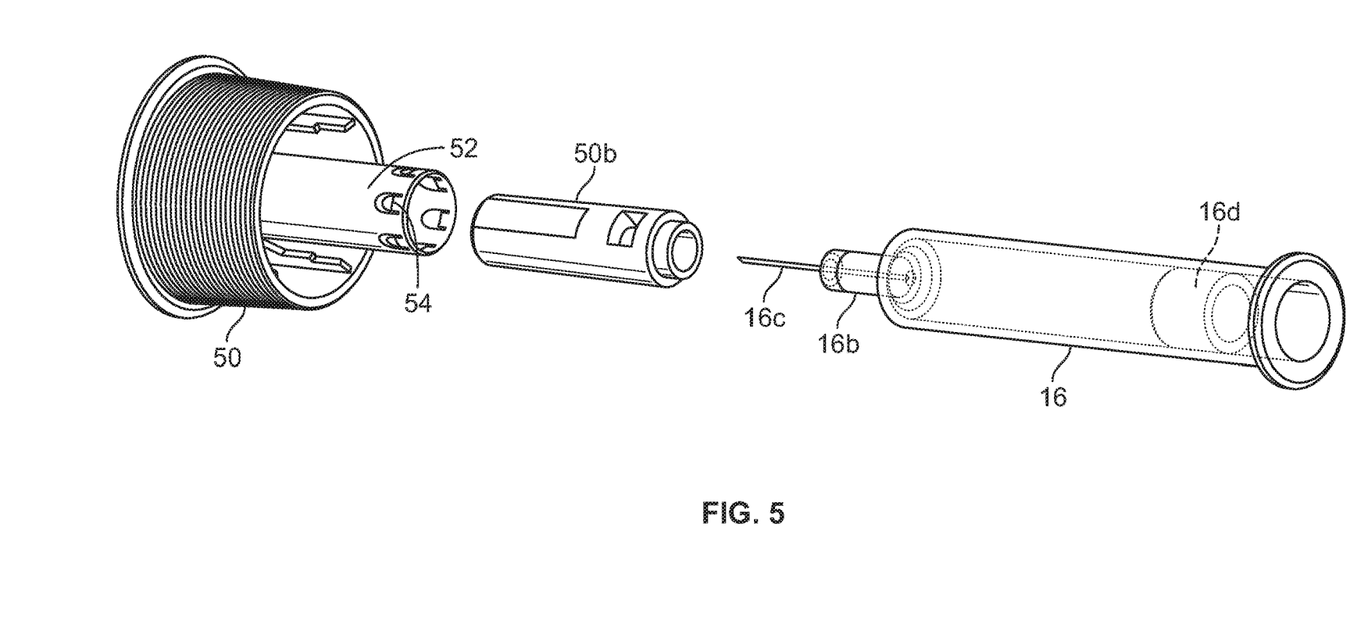
FIG. 5 is an exploded view of the of the needle protection assembly of the drug delivery device of FIG. 1.

A syringe carrier assembly 36, 136 is arranged inside the needle shield 20 and is axially slideable in the proximal proximal direction. Contrary to known single body syringe carrier designs, the present disclosure is directed to a two body design of the syringe carrier assembly, where the two bodies are allowed to move axially relative to each other. In addition to the two bodies, there is also included a force dampener to dissipate excess spring forces at the completion of the penetration and/or injection steps. Two possible designs of the syringe carrier assembly are described below and illustrated in FIGS. 2-4 and 6-8, respectively. The first syringe carrier assembly 36 as shown in FIGS. 2-4 comprises an outer body 57 and an inner body 56, both of which are preferably tubular in shape, with the inner body 56 fitting within, and being slideable relative to the outer body 57. The syringe 16 is positioned within the inner body 56 such that there is no relative axial movement between the syringe and the inner body 56. Plunger 60 is in contact with the stopper 16d of the syringe 16. This contact between the plunger 60 and the stopper 16d prevents the syringe 16 from moving in a distal direction. Also prohibiting movement of the syringe 16 within and relative to the inner body is the pointed tongues 54 that is part of the cap assembly 50. These tongues grab the needle protection shield 50b and assists in holding the syringe 16 in place until cap 50 is removed prior to use of the device. There are no direct attachments or connections between the syringe and the inner body. The proximal end 56c of the inner body 56 is tapered or narrowed to accommodate the proximal end of syringe 16 when it is placed within the inner body 56. The outer body 57 fits over the inner body 56 in a manner that allows relative axial movement between the inner body 56 and the outer body 57.

Because the syringe 16 moves axially with the syringe carrier assembly 36 during the injection process, as described in detail below, at some point in that process the syringe carrier assembly 36 will encounter a hard stop 12b on the inside surface of the front body 12 that stops the forward or proximal movement of the assembly 36. In order to prevent damage to the syringe 16 and/or to prevent the phenomenon of kick-back that can be experienced as an undesirable tactile feeling to the person receiving the injection, it is desirable to provide a force dissipation mechanism to minimize or eliminate these possible negative consequences. In this first embodiment of the syringe assembly 36 the force dampener includes a dampener ring 58 is employed as a third component of this syringe carrier assembly 36. The dampener ring 58 that is fitted over the outside surface 56a of the inner body 56 or alternatively fitted into cup portion 57a at the distal end of outer body 57 and abutting distal facing inner lip 57b. Dampener ring 58 is comprised of a resilient material, preferably a thermoplastic elastomer (TPE), sometimes referred to as thermoplastic rubbers, which are a class of copolymers or a physical mix of polymers (usually a plastic and a rubber) which consist of materials with both thermoplastic and elastomeric properties. Although TPE is the preferred material to use in the manufacture the dampener ring 58 other materials can be used to fabricate the dampener ring 58. Any number of resilient and flexible materials can be used, provided the material can absorb axial forces. The dampener ring 58 is preferably shaped as an annular ring, much like a standard washer, having a central through hole 58a and proximal and distal bearing surfaces 58b & 58c, respectively. The outer diameter 58e of dampener ring 58 should be less than or equal to the largest inner diameter 57c of the outer body 57. The inner diameter of the through hole 58a must be at least as large as the outer diameter 56b of the inner body 56. The thickness 58d of the dampener ring 58 is dependent on the composition of the dampener ring and the desired level of shock dampening, or degree of compression, required to avoid kick-back, damage to the syringe, and/or patient awareness of the completed injection.

As illustrated in FIG. 4, the outer body 57 is a hollow tube having an open proximal end 57d having a diameter 57e large enough to accept the outer diameter 56b of the inner body 56. At the distal end of the outer body 57 is a cup portion 57a that can be formed as an integral part of the outer body during the manufacturing process or can be a separate component that is fixedly attached to the distal end of the outer body. The depth 57f of the cup portion is sized and configured to accommodate the thickness 58d of the dampener ring 58. The outer body 57 also has one or more raised guide surfaces 40 that radially protrude or extend outward from the outer surface 57h and are positioned longitudinally along the outer surface 57h. These guide surfaces 40 interact and cooperate with corresponding shapes of the inner surface of the needle shield 20 in order to obtain a stop means against rotation of the syringe carrier relative the needle shield. Guide surfaces 40 terminate at a proximal end forming a hard stop 40a that engages a corresponding hard stop 12b located on the inside surface of the front body 12 located at the proximal end. The rear or distal end of the outer body 56 is arranged with two rearward directed tongues 42 where each tongue is arranged with an opening 44 and an inwardly directed ledge 46 on the rear edge of each opening. These ledges 46 engage holding member 68.

The inner body 56 is also a hollow tube having tapered or narrowing open proximal end 56c that has an internal shape 56d to accept and hold the proximal end of syringe 16 allowing only the staked needle 16c and/or needle hub assembly 16b to protrude proximally from the inner body 56. (see FIG. 2). The distal end of the inner body 56 terminates in a flange configuration 56e that has a diameter 56f greater than the outer diameter 56b of the inner body. Flange 56e provides a distal bearing surface 56g for abutment with syringe flange 16a and a proximal bearing surface 56h for abutment with the distal bearing surface 58b of the dampener ring 58.

Although the inner body 56 and outer body 57 can move axially relative to each other, the inner and outer bodies are fixed rotationally to each other, i.e., the two bodies cannot rotate relative to each other. This is accomplished by the use of a splined connection 56i and 57g between the two bodies that allows axial movement, but not rotational movement. Preferably, the splined connection comprises one or more, preferably four, raised splines 56i located on the outer surface 56a of the inner body 56 near the distal end. As illustrated in FIG. 4, a preferred shape of these splines 56i is triangular, although other shapes could be used. These raised splines 56i engage and mate with a corresponding number of longitudinal shaped grooves or channels 57g formed on the inside surface of the outer body 57. When engaged the splined connection allows relative axial movement, but not rotation between the inner and outer bodies 56, 57. To prevent axial movement of the dampener ring 58 during assembly of the injection device after the ring 58 has been placed on the outer surface of the inner body 56 or placed in the cup portion of the outer body 57, the splines 56i preferably terminate before the proximal end of the flange 56h thus defining a space or gap 56j that allows the dampener ring 58 to seat itself and to resist axial movement relative to the inner body. The dampener ring 58 is comprised of a material that is resilient enough such that the through hole 58a can stretch or expand sufficiently so that the dampener ring 58 can pass over the splines 56i.

Figure 6:
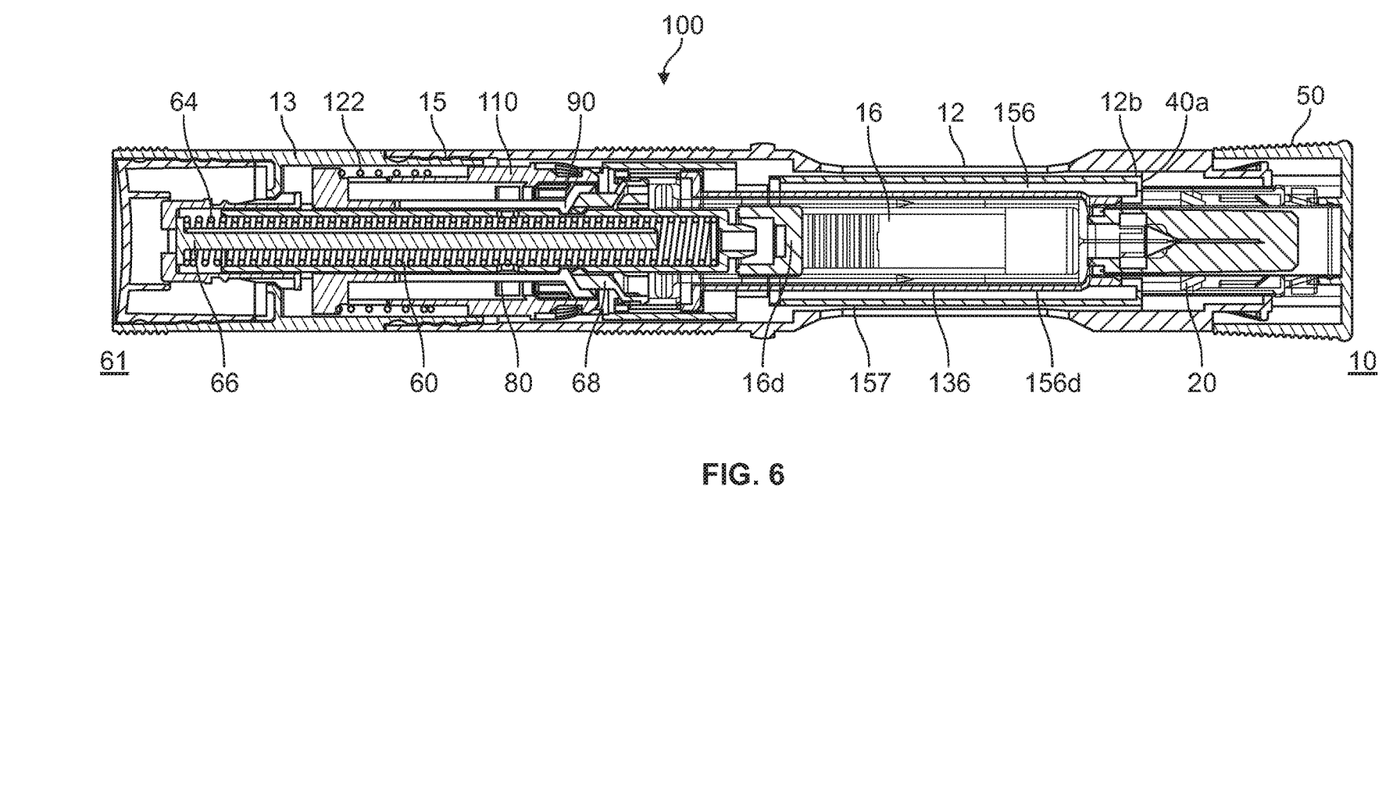
FIG. 6 is a cross-sectional view of the drug delivery device according to FIG. 1 showing a second embodiment of the syringe carrier assembly of the present disclosure.
Figure 7:
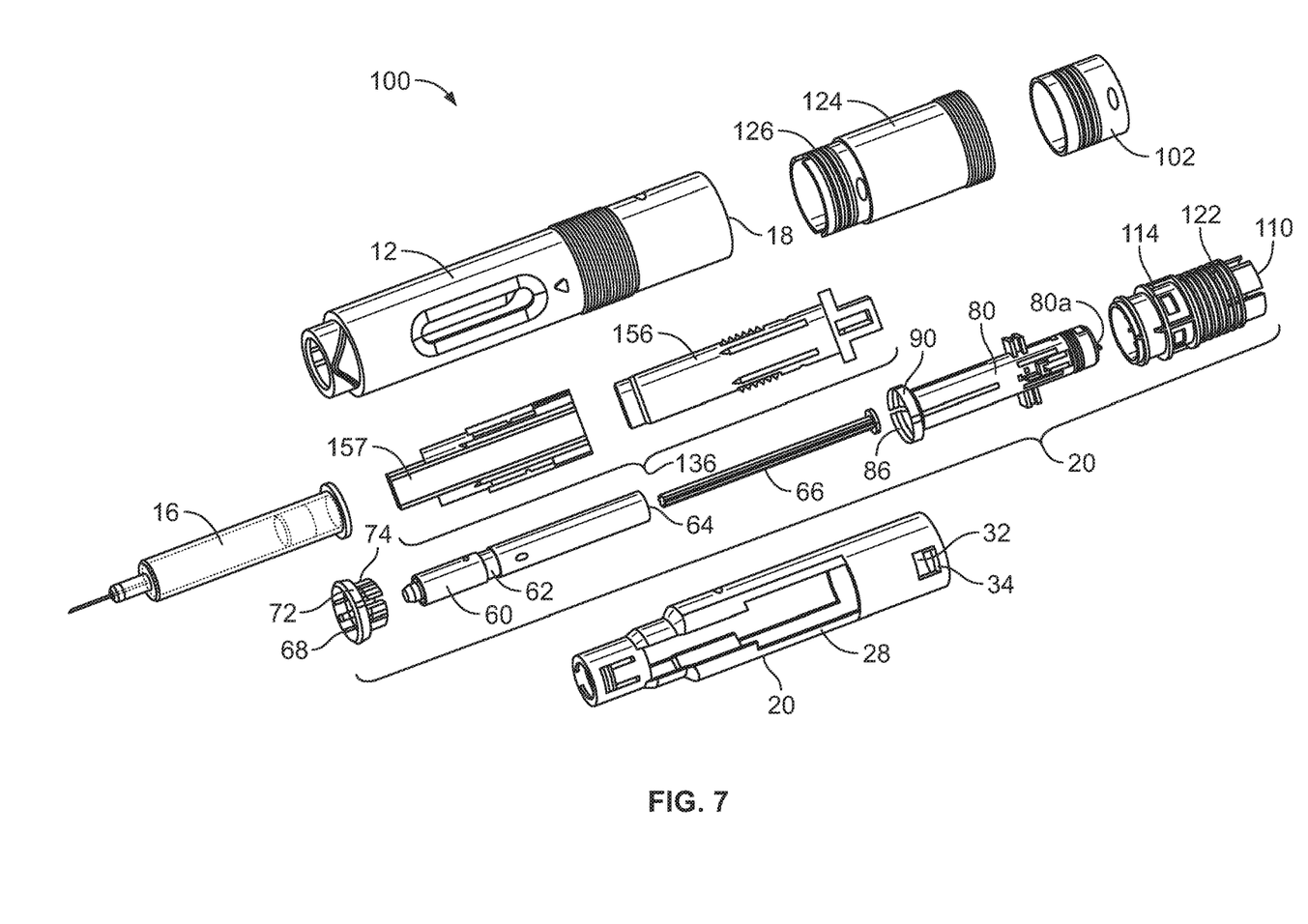
FIG. 7 is an exploded view of the of the drug delivery device shown in FIGS. 1 and 6.
Figure 8:
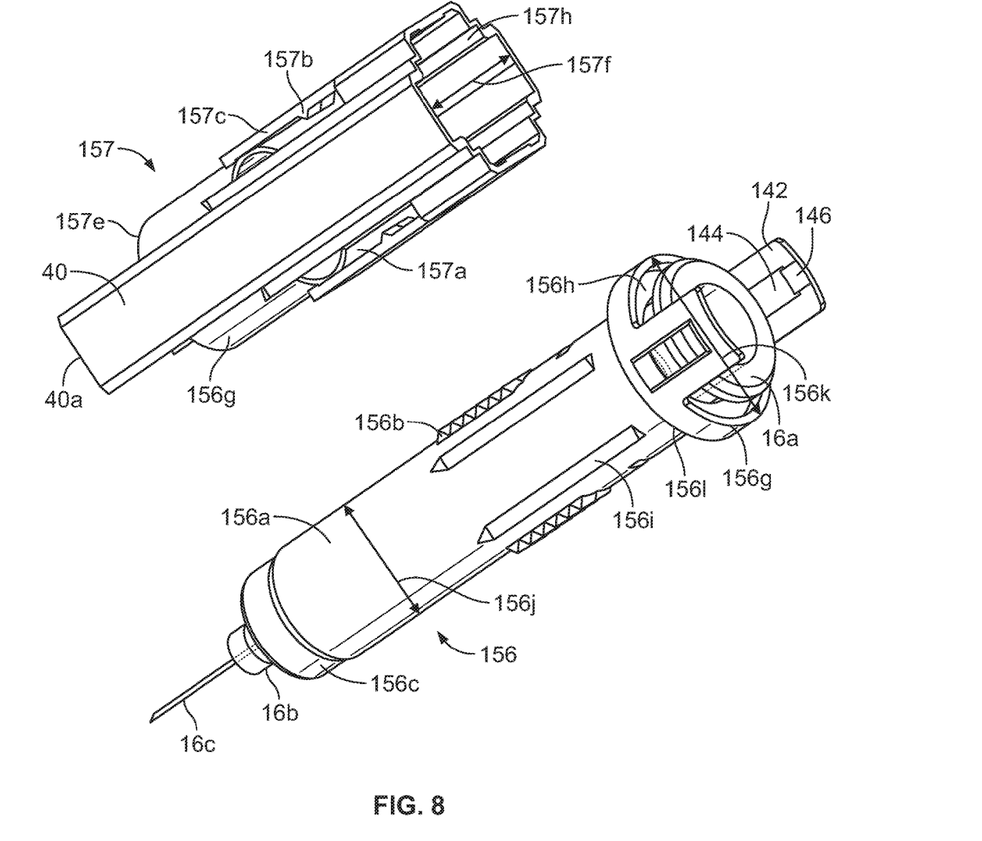
FIG. 8 is an exploded view of the syringe carrier assembly and prefilled syringe of the drug delivery device according to FIG. 6.

A second possible design of the syringe assembly 136 is illustrated in FIGS. 6-8. The syringe carrier assembly 136 is arranged inside the needle shield 20 and is axially slideable in the proximal proximal direction. The second syringe carrier assembly 136 comprises an outer body 157 and an inner body 156, both of which are preferably tubular in shape with the inner body 156 fitted within, and being slidable relative to the outer body 157. The syringe 16 is positioned within the inner body 156 (see FIG. 8) such that there is no relative axial movement between the syringe and the inner body 156. As described above, plunger 60 is in contact with the stopper 16d of the syringe 16. This contact between the plunger 60 and the stopper 16d prevents the syringe 16 from moving in a distal direction. Also prohibiting movement of the syringe 16 within and relative to the inner body is the pointed tongues 54 that is part of the cap assembly 50. These tongues grab the needle protection shield 50b and assists in holding the syringe 16 in place until cap 50 is removed prior to use of the device. There are no direct attachments or connections between the syringe and the inner body. The proximal end 156c of the inner body 156 is tapered or narrowed to accommodate the proximal end of syringe 16 when it is placed with the inner body. The outer body 157 fits over the inner body 156 in a manner that allows relative axial movement between the inner body 156 and the outer body 157.

Because the syringe 16 moves axially with the syringe carrier assembly 136 during the injection process, as described in detail below, at some point in that process the syringe carrier assembly 136 will encounter a hard stop 12b on the inside surface of the front body 12 that stops the forward or proximal movement of the syringe carrier assembly 136. As with the first syringe carrier assembly 36 described above, this second embodiment also has a force dampener to prevent damage to the syringe 16 and/or to prevent kick-back. In this embodiment of the syringe carrier assembly the force dampener includes a flexible ratchet assembly used as a third component of this syringe carrier assembly 136 and comprises a longitudinal array of axial spaced ratchet teeth 156b is formed on the outside surface 156a of inner body 156. Preferably, two or more sets of these spaced ratchet teeth 156b are located at distal end portion of inner body 156. The flexible ratchet further comprises a cooperating ratchet tooth 157b oriented radially inward and supported by flexible rib 157c (see FIG. 8). Preferably, two or more flexible ribs 157c matching the number of number of sets of the axial spaced ratchet teeth 156b can be used. Cut outs or relief lines 157a are used to impart the desired flexibility of the flexible ribs 157c such that the tooth 157b can ride up and over teeth 156b when inner body 156 moves axially in the proximal direction when the outer body 157 encounters the hard stop 12b during operation of the drug delivery device.

As illustrated in FIG. 8, the outer body 157 is a hollow tube having an open proximal end 157e having a diameter 157f large enough to accept the outer diameter 156j of the inner body 156. Preferably, the cross-sectional shape of the hollow portion of the outer body 157 is circular at the proximal end and non-circular at the distal end. The outer body 157 also has one or more raised guide surfaces 40 that radially protrude or extend outward from the outer surface 156g and are positioned longitudinally along the outer surface 156g. These guide surfaces 40 interact and cooperate with corresponding shapes of the inner surface of the needle shield 20 in order to obtain a stop means against rotation of the syringe carrier assembly 136 relative to the needle shield. Guide surfaces 40 terminate at a proximal end forming a hard stop 40a that engages a corresponding hard stop 12b located on the inside surface of the front body 12 located at the proximal end.

The inner body 156 is also a hollow tube having tapered or narrowing open proximal end 156c that has an internal shape 156d to accept and hold the proximal end of syringe 16 allowing only the staked needle 16c or needle hub assembly 16b to protrude proximally from the inner body 156. (see FIG. 8). The distal end of the inner body 156 terminates in a flange configuration 156g that has an outside diameter 156k that is greater than the largest dimension 157f of the distal end of the inner body. Flange 156g contains a step portion that provides a distal bearing surface 156h for abutment with syringe flange 16a. Flange 156g also provides a proximal bearing surface 156l for abutment with the distal end of the outer body 157. The rear or distal end of the inner body 156 is arranged with two rearward directed tongues 142 where each tongue 142 is arranged with an opening 144 and an inwardly directed ledge 146 on the rear edge of each opening 144. These ledges 146 engage the holding member 68.

Although the inner body 156 and outer body 157 can move axially relative to each other, the inner and outer bodies 156, 157 are fixed rotationally to each other, i.e., the two bodies cannot rotate relative to each other. This is accomplished by the use of a splined connection 156i and 157h between the two bodies that allows axial movement, but not rotational movement. Preferably, the splined connection comprises one or more, preferably four, raised splines 156i located on the outer surface 156a of the inner body 156 near the distal end. As illustrated in FIG. 8, a preferred shape of these splines is triangular, although other shapes could be used. These raised splines 156i engage and mate with a correspondingly longitudinal shaped grooves or channels 157h formed on the inside surface of the outer body 157. When engaged, the splined connection allows relative axial movement, but not rotation between the inner and outer bodies.

Attached to the staked needle hub 16b that hold needle 16c of syringe 16 is a needle protection shield 50b that is friction fitted to the staked needle hub 16b of syringe 16. The needle protection shield 50b is surrounded by needle shield grabber 52 having sharp pointed tongues 54 directed somewhat inwards and towards the front or proximal end of the device. The needle shield grabber 52 is operatively connected with cap 50 such that removal of cap 50 results in simultaneous removal of needle protection shield 50b and grabber 52.

FIGS. 3 & 7 shows the rear part or power unit 20 of the injector according to FIG. 1. It comprises a plunger 60 formed as a tube and with an outer diameter somewhat smaller than the inner diameter of the syringe body to be used. The plunger 60 is arranged with a circumferential groove 62 with a certain width. Inside the plunger 60 a helical compression spring 64 is arranged and inside the spring t64 here is a spring guide 66. Adjacent the groove 62 of the plunger 60 a holding member 68 is arranged. It comprises a ring-shaped body having an annular ledge arranged around its circumference and a number of flexible tongues 74 directed towards the rear or distal end of the power unit. Each tongue 74 is arranged with inwardly directed ledges arranged and shaped as to fit into the groove 62 of the plunger 60. Each tongue 74 is further arranged with reinforcing ribs on the outer surfaces.

Surrounding the plunger 60 is an activator 80 with a mainly tubular shape. Its front or proximal end, to the left in the figures, has an inclined transition surface which meets with a band-shaped part with enlarged diameter. On the inner surface adjacent the transition surface an annular inwardly directed ledge 86 is arranged, with a shape as to fit into the groove 62 of the plunger. A number of longitudinally directed cut-outs are arranged at the front part of the actuator 80 so as to form flexible tongues 90. The activator 80 is further provided with two stop ledges directed radially outwards from the outer surface on either side. Between the stop ledges two flexible tongues are arranged on the outer surface. Each tongue is arranged with an outwardly directed hook at the outer end and a protrusion, with an inclined surface, a distance along each tongue. The upper end of the activator 80 is arranged with an end wall 80a. In the injection device embodiment illustrated in FIG. 2b, an activator button 102 is attached to the upper end of the activator 80 having two tongues attached to its outer edge and directed towards the front of the device.

Outside the activator 80 is an actuator sleeve 110 is slidably arranged, also of a generally tubular form. It comprises a front end with a conical part ending in a ledge on its outer surface. At a distance from the ledge a first annular ring is arranged the outer surface. A second annular ring is also arranged a further distance from the ledge. The rear end of the actuator sleeve 110 is arranged with two oppositely arranged cut-outs of a generally rectangular shape where the widths correspond to the width of the stop ledges of the actuator 80. A compression spring 122, hereafter named needle shield spring is surrounding the actuator sleeve.

The previously named components of the power unit are housed in a rear housing 124 of a generally tubular shape, where the front end of the rear housing 124 has a somewhat lesser diameter, corresponding to the inner diameter of the rear end of the front body and provided with a number of annular protrusions 126 which are intended to fit into the corresponding annular recesses 18 on the inner surface of the front body 12. Inside the rear housing 124 an annular ring is arranged, which ring is provided with a circumferential ledge with a shape corresponding to the hooks of the actuator 80. Adjacent the annular ring and in the vicinity of the tongues of the activator button when placed in the housing 13 are arranged inclined surfaces, the function of which will be described below.

The function of the injector according to the invention will now be described with respect to the embodiment shown in FIG. 2b. When assembling the injector the front and the rear parts are assembled individually. As regards the power unit 20 the plunger 60 is held against the force of the compression spring 64 in that the inwardly directed ledges of the tongues 90 of the activator 80 are situated in the groove 62 of the plunger 60 and that the actuator sleeve 110 prevents the tongues 90 from moving outwards. Further the ledges of the holding member are also arranged in the groove 62. The hooks of the activator 80 are adjacent the circumferential ledge as a second safety means should the tongues 90 move out of the groove 62 of the plunger 60. In this position, if the activator button 102 is depressed, it can only move a very short distance inwards together with the actuator 80 until the hooks engage the circumferential ledge.

A syringe 16 is placed in the front end 12 within inner body 56 and rear body 13 is attached to the front body 12 wherein the protrusions 126 fit into the recesses 18. Preferably the syringe 16 is a pre-filled syringe where a medicament is placed within the barrel of the syringe 16 and sealed at the distal end with a slidable stopper or piston 16d. The stacked needle 16c is sealed with the needle protection shield 50b. When the front body 12 and rear body 13 are connected the tongues 34 of the needle shield 20 fit behind the ledge 114 of the actuator sleeve 110 and the ledges 46 of the syringe carrier assembly 36 pass behind the annular ledge 72 of the holding member 68. The needle protection cap 50 with needle shield grabber 52 is inserted into the front end of the device. The device is now ready for use.

When an injection is to be performed the needle protection cap 50 and attached grabber 54 is pulled out of the injector carrying with it the needle protection shield 50b. This causes the sharp pointed tongues 54 to be pushed into the rubber needle protection shield 50b and remove it from the needle hub 16b. The front end of the injector is then pressed against the injection site and the somewhat projecting front end of the needle shield 20 is pushed into the housing 124 against the force of the compression spring 122 acting between the second annular ring of the actuator sleeve and a ledge arranged inside the housing 124. The upper end of the needle shield 20 is in contact with the first annular ring 116 of the actuator sleeve 110 and its movement causes the actuator sleeve 110 to move backwards or distally whereby a part of the band-shaped part is situated outside the front part of the actuator sleeve 110. The upper edge of the actuator sleeve 110 will then come in contact with the inclined surface of the tongues on the actuator 80 whereby the hooks are moved inwards and are free to pass inside the circumferential ledge.

The next step is to activate the penetration and injection. Should the user however remove the injector from the injecting site the compression spring 122 will push the actuator sleeve 110 and thereby the needle shield 20 back to its original position and a press on the button 102 will not cause the device to fire. When activating the penetration and injection, the user merely depresses the activator button 102. This causes the activator 80 to be moved proximally whereby the hooks pass inside the circumferential ledge and the band-shaped part completely out of the actuator sleeve. The resilient properties of the tongues 90 of the activator 80 causes the ledges to move out of the groove 62 of the plunger 60, which then is free to move due to the spring 64. During the movement of the plunger 60, the ledges of the holding member 68 are also moved out of the groove 62 because the arms 74 of the holding member 68 are no longer held in place by the band-shaped part of the activator 80.

In the embodiment shown in FIG. 2a that does not include button 102, the device is activated when the needle shield 20 is pushed against an injection site causing it to retract into the housing 12 in the distal direction. Once fully retracted, the needle shield will engage activator 80 causing the spring 64 to release, firing the device and initiating the injection sequence.

The force of the compression spring 64 urges the plunger 60 to push on the stopper 16d of the syringe. But because of the friction between stopper 16d and syringe barrel inner wall and the incompressibility of the liquid medicament in the syringe and the very small flow passage through the needle, the force will push the syringe 16 and the syringe assembly 36 forward proximally, where needle 16c will penetrate the skin of the patient. The penetration stops when the hard stop 40a of the outer body 57, 157 of the syringe carrier assembly 36, 136 abuts and contacts a ledge or hard stop 12b on the inside surface of the proximal end of the front body 12. Although the outer body 57, 157 encounters the hard stop 40a inside the front body 12 stopping its forward motion, the inner body 56, 156 and the syringe 16 continue to move slightly axially forward (proximally) relative to the outer body 57, 157. In the case of the syringe carrier assembly 36, the dampener ring 58 absorbs the forward momentum compressing slightly and eventually stopping the inner body 56, 156 and the syringe 16. The compression and energy absorbing characteristics of the dampening ring 58 greatly reduces, if not eliminates, the end of injection negative tactile feel experienced by the person receiving the injection. In the case of the syringe carrier assembly 136, as the inner body 156 moves forward relative to the stopped outer body 157, the flexible ratchet assembly absorbs the excess spring force by movement of the longitudinal array of axial spaced ratchet teeth 156b relative to the cooperating ratchet tooth 157b. This movement causes the tooth 157b to ride up and over teeth 156b dissipating the spring force.

The force from the compression spring 64 now moves the stopper 16d inside the syringe and the liquid medicament is injected into the patient until the stopper 16d reaches the inner front end of the syringe barrel. When the plunger has moved this distance, its rear end has passed the ledges of the activator and the tongues are moved inwards. Because the compression spring 64 is also acting on the activator 80, the activator 80 is moved inside the actuator sleeve. Because of this and because the needle shield spring 122 is acting on the actuator sleeve 110 it is urged forward. When now the injector is removed from the injection site, the force of the needle shield spring 122 pushes the actuator sleeve 110 and thus the needle shield 20 connected to it forward, whereby the needle shield 20 is pushed out of the front end of the injector and surrounds the needle 16c. The movement of the actuator sleeve 110 causes the band-shaped part of the actuator 80 to pass ribs arranged on the inner surface of the actuator sleeve 110. These ribs prevent any attempts to push the needle shield 20 back into the injector because the ribs will abut the front end of the band-shaped part of the actuator 80. The needle shield 20 is thus locked, which prevents unintentional needle sticks. The device of FIG. 2b has a safety measure, where it is not possible to first press the activator button 102 and then press the injector against an injection site and release a penetration/injection action because the depression of the activator button causes the hooks to engage the circumferential ledge. Because of the inclined surfaces between the hooks and the circumferential ledge it is not possible to push the tongues inwards by the actuator sleeve 110 acting on the inclined protrusions on the tongues. In order to release a penetration/injection action, the injector has to be pressed first against an injection site in order to be able to depress the activator button and release the plunger 60.

It is to be understood that the embodiments described above and shown in the drawings is to be regarded as a non-limiting example of the invention and that it is defined be the patent claims.

The invention claimed is:

1. A syringe carrier assembly for use in an auto-injector comprising:
   a) an inner body having a proximal end, a distal end and an outer surface, where the inner body is formed as a hollow tubular shape configured to accept and hold a syringe containing medicament, where the hollow tubular shape prevents axial movement of the syringe relative to the inner body;
   b) an outer body with a hollow interior sized to accept and surround the inner body, where the outer body and inner body are slidably connected to each other such that inner body and the outer body are rotationally fixed to each other while allowing relative axial movement; and
   c) a force dampener operatively connected to both the inner body and the outer body to dissipate spring force when the inner body moves axially relative to the outer body and to stop the axial proximal movement of the inner body during a dose delivery operation of the auto-injector.

2. The syringe carrier assembly of claim 1 wherein the force dampener comprises a dampener ring surrounding a portion of the outer surface of the inner body and positioned relative to the outer body such that axial movement of the inner body relative to the outer body causes compression of the dampener ring to stop the axial movement of the inner body and to dissipate the spring force.

3. The syringe carrier assembly of claim 1 further characterized in that the slidable connection comprises cooperation of a raised spline located on one of the inner body and outer body with a correspondingly shaped longitudinal channel on one of the inner body and outer body.

4. The syringe carrier assembly of claim 2 further characterized in that the dampener ring is located at the distal end of the inner body abutting a flange.

5. The syringe carrier assembly of claim 2 further characterized in that outer body has a cup portion at a distal end configured to contain the dampener ring and to prevent the dampener ring from moving axially relative to the inner body.

6. The syringe carrier assembly of claim 2 further characterized in that inner body contains one or more longitudinal splines along the outer surface that terminate prior to a flange located at the distal end of the inner body to define a gap that accepts the dampener ring when positioned on the outer surface abutting the flange.

7. The syringe carrier assembly of claim 6 further characterized in that one or more longitudinal splines mate with cooperating channels located on an inside surface of the outer body to prevent relative rotation, but allow axial movement, between the inner body and the outer body.

8. The syringe carrier assembly of claim 4 further characterized in that the outer body has a cup portion at a distal end configured to contain the dampener ring and having internal diameter greater than an outer diameter of the flange such that the dampener ring and flange fit within the cup portion of the outer body.

9. The syringe carrier assembly of claim 8 further characterized in that the flange is configured as a bearing surface for the syringe.

10. The syringe carrier assembly of claim 1 wherein the force dampener comprises a combination of a longitudinal array of axial spaced ratchet teeth and a flexible rib comprising a ratchet tooth configured to engage with the array of axial spaced ratchet teeth such that axial movement of the inner body relative to the outer body causes the ratchet tooth to ride up and over the array of axial spaced ratchet teeth to dissipate the spring force.

11. The syringe carrier assembly of claim 10 further characterized in that the longitudinal array of axial spaced ratchet teeth is located on the outer surface of the inner body.

12. The syringe carrier assembly of claim 10 further characterized in that the flexible rib is part of the outer body and the ratchet tooth projects radially into the hollow interior.

13. The syringe carrier assembly of claim 10 further characterized in that the distal end of the inner body has a flange containing a step portion that provides a distal bearing surface for abutment with a syringe flange when a syringe is positioned within the inner body.

14. The syringe carrier assembly of claim 13 further characterized in that the flange comprises two distally directed tongues.

15. The syringe carrier assembly of claim 10 further characterized in that inner body contains one or more longitudinal splines along the outer surface that terminate prior to a flange located at the distal end of the inner body, where the splines project radially outward and are triangular shaped to match corresponding triangular shaped channels located on an inside surface of the outer body, where the mating of the splines in the channels prevent relative rotation, but allow axial movement between the inner body and the outer body.

16. A drug delivery device comprising:
   a) an outer housing;
   b) an inner body having a proximal end, a distal end and an outer surface, where the inner body is formed as a hollow tubular shape configured to accept and hold a syringe from axial movement relative to the inner body;
   c) an outer body with a hollow interior sized to accept and surround the inner body, where the outer body and inner body are slidably connected to each other such that inner body and the outer body are rotationally fixed to each other while allowing relative axial movement; and
   d) a force dampener operatively connected to both the inner body and the outer body to dissipate spring force when the inner body moves axially relative to the outer body during a dose delivery operation of the auto-injector; and
   e) a pre-filled syringe containing a dose of medicament positioned within the syringe assembly,
   wherein the inner body and the outer body are completely contained within the outer housing.

17. A method of performing an injection of a dose of medicament comprising:
   a) providing a drug delivery device comprising:
      i) an outer housing;
      ii) an inner body having a proximal end, a distal end and an outer surface, where the inner body is formed as a hollow tubular shape configured to accept and hold a syringe from axial movement relative to the inner body;
      iii) an outer body with a hollow interior sized to accept and surround the inner body, where the outer body and inner body are slidably connected to each other such that inner body and the outer body are rotationally fixed to each other while allowing relative axial movement; and
      iv) a force dampener operatively connected to both the inner body and the outer body to dissipate spring force when the inner body moves axially relative to the outer body and to stop the axial proximal movement of the inner body during a dose delivery operation of the auto-injector; and
      v) a pre-filled syringe containing a dose of medicament positioned within the syringe assembly;
   b) pressing a needle shield positioned within the outer housing against an injection site;
   c) pushing an activation button located at a distal end of the outer housing;
   d) releasing a pre-tensioned compression spring within the outer housing to move the syringe carrier assembly axially in a proximal direction; and
   e) stopping axial movement of the outer body while allowing the inner body to continue moving axially to engage and activate the force dampener.

* * * * *